United States Patent
Falk et al.

[11] Patent Number: 5,225,681
[45] Date of Patent: Jul. 6, 1993

[54] GAS-FILLED UV SPECTROMETER

[75] Inventors: Heinz Falk, Kleve; Ludger Thissen, Bedburg-Hau, both of Fed. Rep. of Germany

[73] Assignee: Spectro Analytical Instruments Gesellschaft fur Analytische Messgerate mbH, Kleve, Fed. Rep. of Germany

[21] Appl. No.: 863,561

[22] Filed: Apr. 3, 1992

[30] Foreign Application Priority Data

May 2, 1991 [DE] Fed. Rep. of Germany ....... 4114276

[51] Int. Cl.[5] .......................... G01J 3/28; F04B 45/00
[52] U.S. Cl. ................................................ 250/372
[58] Field of Search .................. 250/372, 373, 343; 356/51, 346

[56] References Cited

U.S. PATENT DOCUMENTS

| | | | |
|---|---|---|---|
| 3,796,887 | 3/1974 | Vincent et al. | 250/373 X |
| 4,319,843 | 3/1982 | Gornall | 356/346 |
| 4,322,165 | 3/1982 | Ellebracht et al. | 250/372 X |
| 4,596,462 | 6/1986 | Helphrey | 356/244 X |
| 5,091,649 | 2/1992 | Rantala | 250/343 |

OTHER PUBLICATIONS

Milazzo, "Versatile Hollow-Cathode Light Source for Spectrochemical Analysis in the Vacuum Ultraviolet", Applied Spectroscopy, vol. 21, No. 3, 1967, pp. 185-187.

*Primary Examiner*—Constantine Hannaher
*Assistant Examiner*—Edward J. Glick
*Attorney, Agent, or Firm*—Herbert Dubno

[57] ABSTRACT

A UV spectrometer for measurement of spectral intensities over a wavelength range below 190 nm is provided and includes a gas-tight spectrometer vessel, an optical window within the vessel and a UV transparent filling gas inside the vessel. The spectrometer is fitted with a sorption mechanism for binding residual gases that absorbs measuring radiation thereby maintaining the UV transparency of the gas.

10 Claims, 1 Drawing Sheet

GAS-FILLED UV SPECTROMETER

BACKGROUND OF THE INVENTION

1. Field of the Invention

The invention relates to an UV spectrometer for the measurement of spectral intensities in the wavelength range below 190 nm.

2. The Related Art

The UV spectrometer of this invention is equipped with a gas flushing apparatus fitted with a system for minimizing gas consumption. The apparatus is also constructed to prevent the formation of absorbing deposits on optical windows, more particularly on the radiation inlet side, and maintain the partial pressure of absorbing residual gas components at a negligible level. Furthermore, the apparatus according to the invention achieves stable measuring results over a long period of time.

Due to the optical absorption of radiation in the wavelength range below 190 nm by components of the air, spectrometers in vacuum vessels are operated with a residual gas pressure below 1 Pa mbar. Devices for maintaining low pressure within conventional spectrometers are normally quite expensive.

For the spectral range of the so-called vacuum UV, of course, UV-transparent flushing gases are used instead of evacuating the spectrometer to pressures in the range below 10 Pa. The known systems of gas flushing are based on a relatively high gas flow in the range of 30-300 l/h (U.S. Pat. No. 4,322,165), the gas used requiring a very high degree of purity. Similar flow systems with a gas consumption of 5-10 l/h are known from the published literature, for instance, see T. Nakahara and T. Wasa, Applied Spectroscopy, Vol. 41, 1238, 1978; and T. Nakahara, Spectrochim. Acta, Vol. 40B, 293, 1985.

High gas flows are needed to keep residual gases, that arise from desorption and leakage, at a low enough partial pressure. Voluminous pressure gas flasks for flushing renders difficult the practical handling of the apparatuses and is very expensive.

In prior art vacuum spectrometers, dissociation of residual gases contained in the spectrometer vessel has led to formation of absorbing deposits on UV-radiated optical windows and other optical surfaces. As a result, the stability of spectrometric measurements is limited and very expensive maintenance is required. An additional disadvantage of those vacuum spectrometers is the cost of the relatively technologically sophisticated mechanisms required to be built into the instruments to obtain the necessary medium-high vacuum.

Known gas-flushed spectrometers have a relatively high gas consumption of 50-100N m$^3$ per annum at STP and their state of adjustment depends on the external air pressure.

SUMMARY OF THE INVENTION

It is an object of the invention to provide an UV spectrometer in which a constant density of an UV-transparent gas is maintained with minimum gas consumption.

This problem is solved according to the invention through inclusion of a sorption means that can bind residual gases absorbing the measuring radiation in the spectrometer.

The spectrometer, disposed in a gas-tight vessel, is operated at constant gas pressure, which is preferably around 1K Pa above the external pressure. Sorption substances are used to bind residual gases occurring which absorb the radiation to be measured. The sorption substances can be introduced into the spectrometer vessel; alternatively, the filling gas can be circulated via a circulating pump and a flow-sorption cell incorporated in the pump circuit. The sorption means used can be cells based on chemical sorption, adsorption or electrochemical reactions. The flushing gas pressure can be kept constant in the spectrometer vessel within narrow limits by the use of a pressure regulating system comprising a pressure gauge, an electronic control system, an electrically operated valve and a storage vessel. This makes it impossible for the state of adjustment of the spectrometer to be affected by the external air pressure or by possible changes in pressure due to temperature fluctuations.

Since all the components of the spectrometer during operation are at atmospheric pressure, there is minimal degassing resulting in the dirtying of optical components. The excess pressure in the spectrometer vessel ensures that leakages cannot lead to the penetration into the system of optically absorbing components of the surrounding atmosphere. The pressure regulating system according to the invention reduces the gas consumption of the instrument to very low values so that, for example, a quantity of gas less than 50 l per annum at STP is adequate for the operation of the spectrometer. The apparatus can therefore be regarded as practically autonomous as regards replacement of the flushing gas.

Repeated passage of the flushing gas through the purification cell leads to a substantial degassing of the surface and incorporated parts inside the vacuum vessel. Maximum optical transmission can therefore be achieved even in the range below 180 nm.

BRIEF DESCRIPTION OF THE DRAWING

An embodiment of the invention will now be described in greater detail with reference to the drawing constituted of a sole FIGURE which is a highly schematic representation of the spectrometer illustrating the various functional elements.

DETAILED DESCRIPTION OF THE INVENTION

Figure 1:
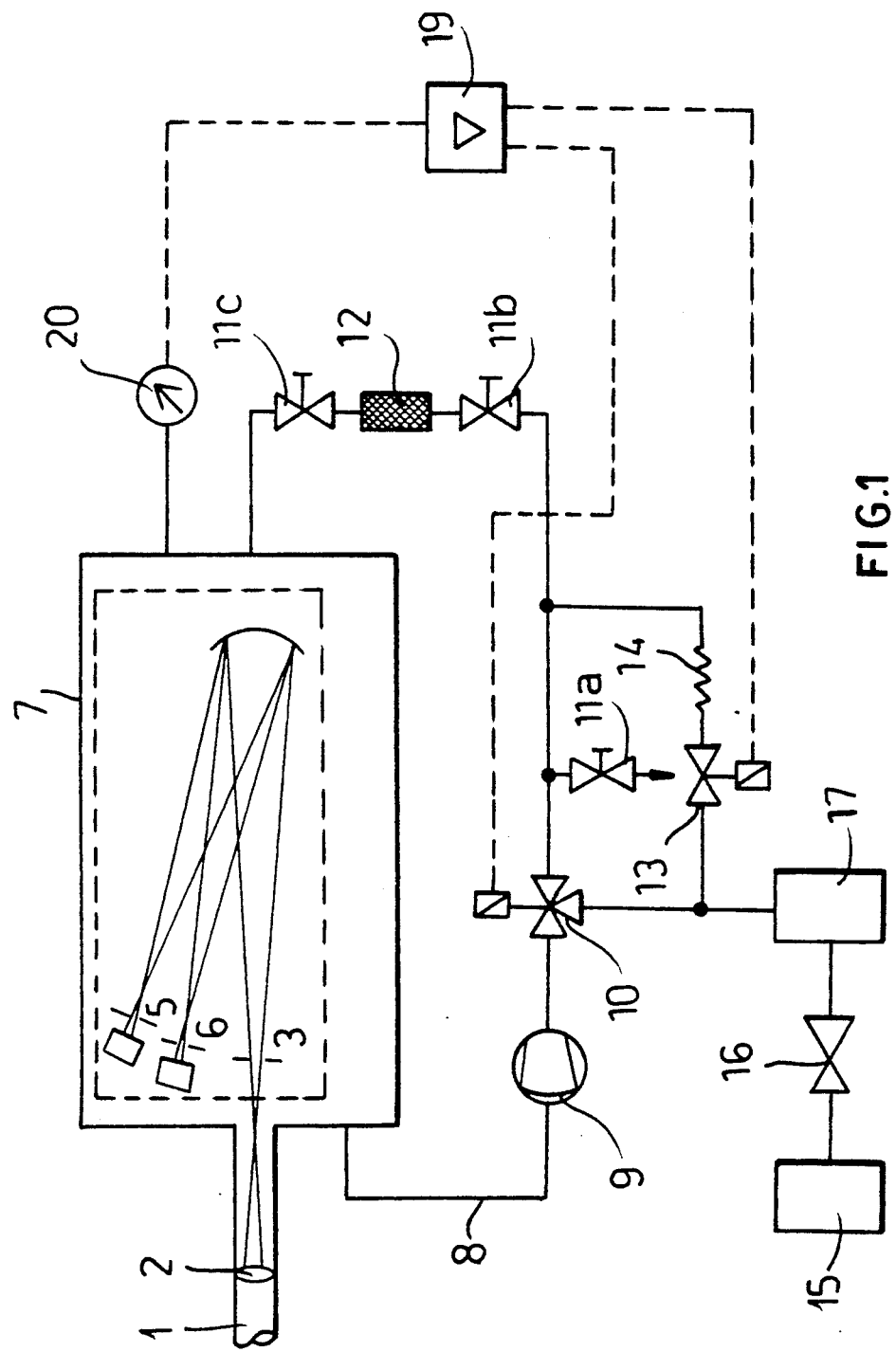

FIG. 1 shows an embodiment of the apparatus according to the invention, with gas pressure regulation and a gas refilling device, and a UV polychromator. The optical system of the apparatus is disposed in a gas-tight vessel. The system includes an inlet pipe (1), an imaging lens (2) acting as an entrance window, an entrance slit (3), a diffraction grating (4), an exit slit (5) and a radiation receiver (6). Evacuation of gas from the system occurs via a gas pipe (8) by means of a membrane pump (9) with a flow valve (11a) opened. A purification cell (12) is closed by the closure of flow valves (11b+11c). A flow valve (13) is also closed. When a sufficiently low residual gas pressure has been reached, with the pump switched off, the spectrometer vessel (7) is filled with gas from a supply tank (15) by the opening of the valve (13). The pumping-out and subsequent filling of the spectrometer vessel can be repeated, to obtain a low partial pressure of residual gas components. Advantageously, filling is performed after venting of the spectrometer vessel (7) by repeated partial evacuation by means of the circulating pump (9) followed by filling with gas and the removal of the residual gas via the purification cell (12).

To obtain a clearly-defined excess pressure of the UV-transparent flushing gas inside the spectrometer vessel (7), the valve (13) is opened and by means of a pressure gauge (20) via an electronic control device (19) the pressure is measured until the required pressure is reached. As it is being supplied, the filling gas is circulated by means of the pump (9) and the flow position of a three-way valve (10) is oriented in the direction of the purification cell (12). Even during the operation of the spectrometer, the pump (9) remains switched on, so that desorbed residual gas components are removed by means of the purification cell (12). The purification cell (12) can contain, for example, copper oxide on a silica gel support and suitable molecular sieve absorbers as granulates.

If gas losses take place due to the apparatus leaking, so that the pressure drops below a given required value, the gas is supplemented via the electronic control device (19) by the opening of the valve (13).

Temperature changes in the spectrometer vessel lead to an increase in pressure in the system, possibly resulting in changes in the state of adjustment of the spectrometer. The pressure in the spectrometer vessel is therefore maintained below a preselected limit by the three-way valve (10) being opened in the direction of a storage tank (17) when the pressure rises. This position of the three-way valve (10) is maintained until the resulting gas surplus has been pumped into the storage tank (17). Thereafter a changeover back to gas circulating operation is made by changing over the three-way valve (10). When the temperature drops, gas from the storage tank enters the installation, as already mentioned hereinbefore, via valve (13). A flow resistance (14) ensures against abrupt pressure changes. By a regulating valve (16) a minimal excess pressure is always maintained in the storage tank (17), so that gas losses due to leakage are compensated for in this manner. The flushing gases used can be nitrogen, argon or helium, in dependence on the required spectral range.

The arrangement illustrated in FIG. 1 can be simplified when the properties of the spectrometer do not require pressure regulation. In that case use is made of merely a circulating pump and a purification device in the outer gas circuit.

We claim:

1. A UV spectrometer for measurement of spectral intensities over a wavelength range below 190 nm comprising:
   a gas-tight spectrometer vessel;
   at least one optical window within said vessel;
   a UV transparent filling gas inside said vessel; and
   sorption means for the purpose of binding residual gases that absorb measuring radiation in said spectrometer and said means arrangedly communicating with said spectrometer vessel to accomplish said purpose.

2. A UV spectrometer according to claim 1 further comprising a pressure regulating system for maintaining a constant pressure of said filling gas inside said vessel which is higher than external air pressure.

3. A UV spectrometer according to claim 2 further comprising a gas circuit external to said vessel, said sorption means including a sorption substance, said circuit containing therewithin said sorption substance and fitted with a circulating pump; said filling gas being continuously circulated by means of said pump through said vessel.

4. A UV spectrometer according to claim 3 wherein said gas circuit forms part of said pressure regulating system, said system further comprising a means for measuring gas pressure in said vessel and a means for adjusting pressure in said vessel in response to the measured pressure.

5. A UV spectrometer according to claim 4 wherein said means for adjusting pressure is a three-way valve which, positioned at an outlet of the circulating pump, can be switched to have said vessel communicate with a storage tank for supplying gas.

6. A UV spectrometer according to claim 4 wherein said means for adjusting pressure is a controllable valve which supplies a gas from a storage tank to said gas circuit.

7. A UV spectrometer according to claim 6 further comprising a gas supply tank communicating via a pressure regulating valve with said storage tank thereby functioning to compensate for any gas losses.

8. A UV spectrometer according to claim 1 wherein said sorption means for binding residual gases is placed directly into said vessel.

9. A UV spectrometer according to claim 1 wherein said sorption means comprises an electrochemical gas-consuming cell.

10. A UV spectrometer according to claim 3 wherein said circulating pump is a membrane pump.

* * * * *